(12) United States Patent
Albrecht et al.

(10) Patent No.: US 10,258,634 B2
(45) Date of Patent: Apr. 16, 2019

(54) CICLESONIDE FOR THE TREATMENT OF AIRWAY DISEASE IN HORSES

(71) Applicant: Boehringer Ingelheim Vetmedica GmbH, Ingelheim am Rhein (DE)

(72) Inventors: Balazs Albrecht, Sprendlingen (DE); Michael Aven, Mainz (DE); Janine Lamar, Ingelheim am Rhein (DE); Ingo Lang, Ingelheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 42 days.

(21) Appl. No.: 15/292,765

(22) Filed: Oct. 13, 2016

(65) Prior Publication Data

US 2017/0079988 A1    Mar. 23, 2017

Related U.S. Application Data

(63) Continuation of application No. 14/132,580, filed on Dec. 18, 2013, now abandoned.

(30) Foreign Application Priority Data

Dec. 21, 2012  (EP) .................................... 12199302

(51) Int. Cl.
 *A61K 31/58* (2006.01)
 *A61K 9/00* (2006.01)

(52) U.S. Cl.
 CPC .............. *A61K 31/58* (2013.01); *A61K 9/008* (2013.01); *A61K 9/0073* (2013.01); *A61K 9/0078* (2013.01)

(58) Field of Classification Search
 CPC ..................................................... A61K 31/58
 USPC ......................................................... 514/174
 See application file for complete search history.

(56) References Cited

U.S. PATENT DOCUMENTS

| | | | |
|---|---|---|---|
| 5,823,179 A | 10/1998 | Grychowski et al. | |
| 5,954,049 A | 9/1999 | Foley et al. | |
| 6,264,923 B1 | 7/2001 | Oliver et al. | |
| 6,706,726 B2 | 3/2004 | Meissner et al. | |
| 7,244,742 B2 | 7/2007 | Pieper et al. | |
| 7,829,748 B1* | 11/2010 | Tung ........................ | B01J 27/10 570/153 |
| 2003/0234015 A1 | 12/2003 | Bruce et al. | |
| 2004/0266869 A1 | 12/2004 | Montague et al. | |
| 2006/0069073 A1 | 3/2006 | Pieper et al. | |
| 2006/0110329 A1 | 5/2006 | Pieper | |
| 2006/0293293 A1 | 12/2006 | Muller et al. | |
| 2007/0025923 A1 | 2/2007 | Wurst et al. | |
| 2007/0117783 A1 | 5/2007 | Brueck-Scheffler | |
| 2007/0134165 A1 | 6/2007 | Wurst et al. | |
| 2008/0041369 A1 | 2/2008 | Radau et al. | |
| 2008/0041370 A1 | 2/2008 | Radau et al. | |
| 2012/0039817 A1 | 2/2012 | Vehring et al. | |
| 2012/0058980 A1 | 3/2012 | Radau et al. | |
| 2014/0116427 A1 | 5/2014 | Pevler et al. | |
| 2014/0179650 A1 | 6/2014 | Aven et al. | |
| 2014/0179651 A1 | 6/2014 | Albrecht et al. | |
| 2015/0053202 A1 | 2/2015 | Knell et al. | |
| 2015/0053203 A1 | 2/2015 | Knell et al. | |
| 2015/0202148 A1 | 7/2015 | Cifter et al. | |
| 2015/0202297 A1 | 7/2015 | Cifter et al. | |
| 2015/0366855 A1 | 12/2015 | Albrecht et al. | |
| 2017/0007593 A1 | 1/2017 | Albrecht et al. | |

FOREIGN PATENT DOCUMENTS

| | | |
|---|---|---|
| CA | 2495454 A1 | 3/2004 |
| WO | 1997012687 A1 | 4/1997 |
| WO | 200232899 A1 | 4/2002 |
| WO | 2004022058 A1 | 3/2004 |
| WO | 2004023984 A2 | 3/2004 |
| WO | 2005009426 A1 | 2/2005 |
| WO | 2006056527 A1 | 6/2006 |
| WO | 2010149280 A1 | 12/2010 |
| WO | 2014096115 A1 | 6/2014 |
| WO | 2015193213 A1 | 12/2015 |

OTHER PUBLICATIONS

Weinbrenner et al., "Circadian Rhythm of Serum Cortisol after Repeated Inhalation of the New Topical Steroid ciclesonide". The Journal of linical Endocrinology & Metabolism, vol. 87, No. 5, pp. 2160-2163.
Derom et al., "Effects of inhaled ciclesonide and fluticasone propionate on cortisol secretion and airway responsiveness to adenosine 5' monophosphate in asthmatic patients." Pulmonary Pharmacology & Therapeutics, vol. 18, 2005, pp. 328-336.
U.S. Appl. No. 14/654,009, filed Jun. 19, 2015, now U.S. Pat. No. 9,918,995.
U.S. Appl. No. 15/889,307, filed Feb. 6, 2018.
"Public Assessment Report: Mutual Recognition Procedure". MHRA, PAR Alvesco/Freathe/Amavio 40, 80 and 160 Inhaler, Nycomed GmbH, 2008, pp. 1-61.
Belvisi et al., "Preclinical Profile of Ciclesonide, a Novel Corticosteroid for the Treatment of Asthma". The Journal of Pharmacology and Experimental Therapeutics, vol. 314, No. 2, 2005, pp. 568-574.
Couetil et al., "Inflammatory Airway Disease of Horses"., Journal of Veterinary Internal Medicine, vol. 21, 2007, pp. 356-361.
Dauvillier et al., "Effect of Long-Term Fluticasone Treatment on Immune Function in Horses with Heaves". Journal of Veterinary Internal Medicine, vol. 25, No. 3, 2011, pp. 549-557.
Dietzel et al., "Ciclesonide: An On-Site-Activated Steroid". New Drugs for Asthma, Allergy and COPD. Progress in Respiratory Research, Basel, Karger, vol. 31, 2001, pp. 91-93.
Dubuc et al., "Airway wall eosinophilia is not a feature of equine heaves". The Veterinary Journal, vol. 202, 2014, pp. 387-389.
International Search Report and Written Opinion for PCT/EP2013/077264 dated Feb. 3, 2014.
Kutasi et al., "Diagnostic Approaches for the Assessment of Equine Chronic Pulmonary Disorders". Journal of Equine Veterinary Science, vol. 31, 2011, pp. 400-410.

(Continued)

*Primary Examiner* — Jennifer M Kim
(74) *Attorney, Agent, or Firm* — Judy Jarecki-Black

(57) ABSTRACT

The invention relates to the field of medicine, in particular to the field of veterinary medicine. The invention relates to glucocorticoids, especially ciclesonide or a pharmaceutically acceptable derivative or salt thereof, for the treatment of airway disease in horses, such as pulmonary disease, preferably recurrent airway obstruction (RAO), Summer Pasture Associated Obstructive Pulmonary disease (SPAOPD), and inflammatory airway disease (IAD).

27 Claims, 9 Drawing Sheets

(56) References Cited

OTHER PUBLICATIONS

Lavoie et al. "Comparison of effects of dexamethasone and the leukotriene D4 receptor antagonist L-708,738 on lung function and airway cytologic findings in horses with recurrent airway obstruction". American Journal of Veterinary Research, vol. 63, No. 4, Apr. 2002, pp. 579-585.
Lavoie et al. "Effects of a MAPK p38 inhibitor on lung function and airway inflammation in equire recurrent airway obstruction". Equine Veterinary Journal, vol. 40, No. 6, 2008, pp. 577-583.
Lavoie et al., "Lack of Clinical Efficacy of a Phosphodiesterase-4 Inhibitor for Treatment of Heaves in Horses". Journal of Veterinary Internal Medicine, vol. 20, 2006, pp. 175-181.
Matera et al., "Innervation of Equine Airways". Pulmonary Pharmacology & Therapeutics, vol. 15, 2002, pp. 503-511.
Moran et al., "Recurrent airway obstruction in horses—an allergic inflammation: a review". Veterinami Medicinia, vol. 56, 2011, pp. 1-13.
Mutch et al., "The role of esterases in the metabolish of cidesonide to desisobutyryl-ciclesonide in human tissue". Biochemical Pharmacology, vol. 73, 2007, pp. 1657-1664.
Robinson et al., "Fluticasone Propionate Aerosol is More Effective for Prevention than Treatment of Recurrent Airway Obstruction". Journal of Veterinary Internal Medicine, vol. 23, 2009, pp. 1247-1253.
Robinson et al., "The airway response of horses with recurrent airway obstruction (heaves) to aerosol administration of ipratropium bromide". Equine Veterinary Journal, vol. 25, No. 4, 1993, pp. 299-303.
Robinson, N.E., "International Workshop on Equine Chronic Airway Disease. Michigan State University, Jun. 16-18, 2000". Equine Veterinary Journal vol. 33, No. 1, 2001, pp. 5-19.

\* cited by examiner

CICLESONIDE FOR THE TREATMENT OF AIRWAY DISEASE IN HORSES

CROSS REFERENCE TO RELATED APPLICATIONS

This application is a continuation of, and claims benefit of, U.S. patent application Ser. No. 14/132,580, filed Dec. 18, 2013, now abandoned, which claims priority to European Application No. 12199302.6, filed Dec. 21, 2012.

FIELD OF THE INVENTION

The invention relates to the field of medicine, in particular to the field of veterinary medicine. The invention relates to glucocorticoids or inhaled glucocorticoids, especially ciclesonide or a pharmaceutically acceptable derivative thereof, for the treatment of airway disease in horses, such as pulmonary disease, preferably recurrent airway obstruction (RAO), summer pasture associated obstructive pulmonary disease (SPAOPD), and inflammatory airway disease (IAD).

BACKGROUND INFORMATION

Equine airway disease is a prominent disease in many horses. It can be divided into the diseases of the upper and lower airways. There are a number of equine lower airway diseases with noninfectious origin such as RAO (or heaves or equine chronic obstructive pulmonary disease), IAD, SPAOPD and exercise induced pulmonary hemorrhage (EIPH). The latter is typically diagnosed in racehorses. RAO, IAD and SPAOPD are diseases with an allergic background. Rarely diagnosed additional lower airway disorders are granulomatous, neoplastic and interstitial pneumonias. The infectious diseases of the lower airway include bronchitis, pneumonia, pleuritis or a combination of these caused by viral, bacterial, fungal and parasitic agents (Kutasi et al., 2011, hereby incorporated by reference).

Common phenotypic manifestations of airway disease in horses include coughing, nasal discharge, increased respiratory effort and poor performance or exercise intolerance. Additionally, fever, depression, decreased appetite and weight loss can be observed in infectious airway diseases (Couetil et al., 2007 and Kutasi et al., 2011, hereby incorporated by reference).

Equine airway diseases with an allergic background cannot be cured but only kept asymptomatic. The known therapies for these horses include changes in the environment and the administration of different drugs. The aim of the change in the stable environment is to improve airway quality and to reduce the allergen exposure of the horses, which might trigger the exacerbations of RAO, SPAOPD and IAD. The following drugs are used for the treatment of airway diseases with noninfectious origin: glucocorticoids, bronchodilators (β2 agonists and anticholinergic agents), and mucosolvants (dembrexin and acetylcystein). In addition, antibiotics are administered for infectious airway diseases. Prominent side effects of these standard therapies are tachycardia, mydriasis, and colic for bronchodilators and adrenocortical suppression (reduction in the blood serum levels of cortisol), laminitis, hepatopathy, muscle wasting, altered bone metabolism, increased susceptibility to infection (neutrophilia, lymphopenia) and decreased antibody response to vaccination for glucocorticoids (Couetil et al., 2007, Dauvillir et al., 2011, hereby incorporated by reference).

The problem underlying the present invention is to provide a medication for horses which allows the treatment of airway disease in horses while reducing the risk of side effects for the treated animals.

BRIEF SUMMARY OF THE INVENTION

It has been surprisingly found that ciclesonide or a pharmaceutically acceptable salt thereof or a composition comprising ciclesonide or a pharmaceutically acceptable salt thereof is particularly advantageous for the use in a method of treating an airway disease in equines, preferably horses. An advantage of the present invention is the absence or reduction of side effects. The administration of glucocorticoids can decrease the production of cortisol by the hypothalamic-pituitary-adrenal (HPA) axis. Thus, measurement of serum cortisol level is generally used as surrogate marker of glucocorticoid systemic activity and a tool for assessing systemic bioavailability of glucosorticoids. Such a reduction of equine serum cortisol levels occurs in state of the art treatment options including drug administration via a peroral or parenteral (e.g. dexamethasone, prednisone) as well as via an inhalative (beclomethasone, fluticasone proprionate and budesonide) route. In contrast, no decrease in the serum cortisol level of horses is observed after treatment for two weeks with different dose levels of ciclesonide (see Examples 2-3).

In addition, the treatment option provided by the present invention minimizes the risks associated with complications caused by altered metabolism or compromised immune system, etc. Neutrophilia and lymphopenia is commonly observed after the state of the art treatment with dexamethasone (see example 4, Table 2). This can lead to increased susceptibility to infections. In contrast, no alteration is observed in the immune system of horses measured by neutrophilia and lymphopenia after treatment for two weeks with different dose levels of ciclesonide (see example 4, Table 2).

Another advantage of the present invention is treatment convenience. The state of the art treatment with dexamethasone does not allow the administration of constantly high dose levels for a longer time period due to the risk of developing side effects. Therefore, the dose of dexamethasone has to be continuously adjusted after treatment initiation considering a number of factors (e.g. route of drug administration, medical history, clinical condition and body weight of the horse) with the aim to prevent or minimize side effects while administering a high enough dose for assuring clinical efficacy. In contrast, the present invention provides a superior treatment option for horses with a lower risk for developing side effects. Thus, it does allow for a treatment over long periods of time at constantly high dose levels with assuring the required clinical efficacy, which is comparable to dexamethasone.

Furthermore, the safety profile of ciclesonide is also more advantageous compared to other aerosol glucocorticoids like fluticasone proprionate. There are conflicting reports about the effect of fluticasone proprionate on cortisol levels. In some studies fluticasone proprionate shows significant suppression in measured cortisol levels in both humans and horses after aerosol administration (Robinson et al., 2009 and Grahnén et al., 1997). In contrast, there is no or clinically not relevant cortisol suppression with ciclesonide in humans or in horses after aerosol inhalation.

An additional advantage of the present invention is the prodrug nature of ciclesonide. It has been shown that the active metabolite, C21-C21-desisobutyrylciclesonide, is generated in the airways of humans or other mammals. The prodrug ciclesonide has to be activated by special enzymes in the airway tissues in order to generate C21-21-desisobutyrylciclesonide, which is the effective molecule. The existence of such special enzymes in the equine airway tissues has not been previously reported. Other substances like fluticasone proprionate, which is not a prodrug, do not need enzymatic conversion to be able to be active in the lungs of horses or other mammals. The present invention surprisingly demonstrates for the first time that ciclesonide can be converted into the effective molecule C21-C21-desisobutyrylciclesonide in horses (please see example 5) and that ciclesonide administration thus results in a beneficial therapeutic effect in horses with airway disease.

Furthermore, ciclesonide undergoes reversible fatty acid esterifications with fatty acids in human lung tissue. The fatty acid conjugates may serve as a depot. It has not been previously reported whether the same esterification process occurs in equine lung tissues as well or not. Other substances like fluticasone proprionate do not generate fatty acid conjugates in human lung tissues at all.

Therefore, even if large amounts of ciclesonide are swallowed during aerosol treatment the prodrug nature of ciclesonide, the dependency of C21-C21-desisobutyrylciclesonide generation on specific enzyme conversion and a quick liver metabolism of C21-C21-desisobutyrylciclesonide assures that the effect of ciclesonide is only related to the airways and not to the whole body of the horses. This is also referred to as topic effect of ciclesonide. In contrast, the state of the art treatment with dexamethasone or other substances like fluticasone leads to a systemic exposure of the active metabolite, leading to an extensive side effect profile.

The present invention concerns ciclesonide or a pharmaceutically acceptable salt thereof or a composition comprising ciclesonide or a pharmaceutically acceptable salt thereof for use as a medicament for treating an equine, preferably a horse. The present invention concerns ciclesonide or a pharmaceutically acceptable salt thereof or a composition comprising ciclesonide or a pharmaceutically acceptable salt thereof for use in a method of treating an equine, preferably a horse.

The present invention concerns ciclesonide or a pharmaceutically acceptable salt thereof or a composition comprising ciclesonide or a pharmaceutically acceptable salt thereof for the use in a method of treating an airway disease in equines, preferably horses. The present invention concerns ciclesonide or a pharmaceutically acceptable salt thereof or a composition comprising ciclesonide or a pharmaceutically acceptable salt thereof for the use in a method of treating (an) airway disease(s) in (an) equine(s), preferably in (a) horse(s).

According to a specific aspect of the present invention said ciclesonide or said pharmaceutically acceptable salt thereof or said composition comprising ciclesonide or said pharmaceutically acceptable salt thereof is inhalable/(in the form of) an inhalant. In another aspect of the present invention the ciclesonide or the pharmaceutically acceptable salt thereof or the composition comprising ciclesonide or the pharmaceutically acceptable salt thereof is in a liquid formulation, preferably an ethanolic formulation, which can be aerosolized to facilitate its inhalation. In a further aspect of the present invention the liquid formulation is partially ethanolic and partially aqueous. In a further aspect of the present invention the liquid formulation comprises one or more of the solvents: water, ethanol, hydrofluoroalkane(s) such as HFA 227 and HFA 134a, hydrofluoroolefin(s) such as HFO-1234ze, and optionally additional excipients. HFA is short for hydrofluoroalkane and HFO is the abbreviation for hydrofluoroolefin.

In a preferred aspect of the present invention the solvent of the liquid formulation comprises/consists of a mixture of ≥85% V/V ethanol and ≤15% V/V water, such as for example 10% V/V aqueous and 90% V/V ethanol.

In another preferred aspect of the present invention the solvent of the liquid formulation comprises a mixture of ethanol and water, whereby the proportion of ethanol is in the range of 85-100% V/V, preferably 90-95% V/V. Preferably the proportion of ethanol is 90% V/V ethanol.

In a specific aspect of the present invention the formulation (inhalation solution) of ciclesonide is as follows:

TABLE 1

| Ingredient | Content |
| --- | --- |
| Ciclesonide | 0.7-3.1 g/100 mL |
| Hydrochloric acid | ad [H$^+$] = 10$^{-3.5}$ to 10$^{-5}$ mol/L |
| 90% V/V ethanol/water | ad 100 ml | where the concentration of hydrogen ions [H$^+$] can be measured, for example, by potentiometric titration.

A further aspect of the present invention is the application of the liquid formulation using an inhalation device, such as the RESPIMAT® inhaler or another inhalation device using the RESPIMAT® aerosol-generating technology. The RESPIMAT® inhaler is disclosed for example in WO 97/12687, which is hereby incorporated by reference. This inhaler can advantageously be used to produce the inhalable aerosols/inhalants according to the invention. The dose of active substance delivered ex RESPIMAT® inhaler can be calculated from:

the concentration of active substance in the liquid formulation (inhalation solution) [µg/µl],
the "delivered volume", defined as the volume of liquid expelled from the RESPIMAT® inhaler per actuation M. The delivered volume ex RESPIMAT® inhaler has been found to be approximately 11.05 µl per actuation, according to the following formula:

Dose [µg]=Concentration [µg/µl]·Delivered Volume [µl]

The invention further concerns ciclesonide or a pharmaceutically acceptable salt thereof or a composition comprising ciclesonide or a pharmaceutically acceptable salt thereof for the use (in a method) for the management/treatment of airway disease in equines, preferably horses. Preferably the airway disease is a pulmonary disease. The invention further concerns ciclesonide or a pharmaceutically acceptable salt thereof or a composition comprising ciclesonide or a pharmaceutically acceptable salt thereof for the use (in a method) for the management/treatment of recurrent airway obstruction (RAO) in equines, preferably horses. The invention further concerns ciclesonide or a pharmaceutically acceptable salt thereof or a composition comprising ciclesonide or a pharmaceutically acceptable salt thereof for the use (in a method) for the management/treatment of summer pasture associated obstructive pulmonary disease (SPAOPD) in equines, preferably horses. The invention further concerns ciclesonide or a pharmaceutically acceptable salt thereof or a composition comprising ciclesonide or a pharmaceutically acceptable salt thereof for the use (in a method) for the management/treatment of inflammatory airway disease (IAD) in equines, preferably horses.

The invention further concerns a method of treating an airway disease comprising administering a therapeutic effective amount of ciclesonide or a pharmaceutically acceptable salt thereof or a composition comprising ciclesonide or a pharmaceutically acceptable salt thereof to an equine patient, preferably a horse, in need thereof. Preferably the airway disease is a pulmonary disease. In a specific aspect of said method of treatment of the present invention ciclesonide or a pharmaceutically acceptable salt thereof or a composition comprising ciclesonide or a pharmaceutically acceptable salt thereof is administered as an inhalable/inhalant. In a further specific aspect of the method of treatment of the present invention ciclesonide or a pharmaceutically acceptable salt thereof or a composition comprising ciclesonide or a pharmaceutically acceptable salt thereof is in a liquid formulation, preferably with a solvent comprising/consisting of ethanol, water or a combination thereof. In another aspect of the method of treatment of the present invention ciclesonide or a pharmaceutically acceptable salt thereof or a composition comprising ciclesonide or a pharmaceutically acceptable salt thereof is administered via an (equine) inhalation device. In a preferred aspect of the method of treatment of the present invention ciclesonide or a pharmaceutically acceptable salt thereof or a composition comprising ciclesonide or a pharmaceutically acceptable salt thereof is in a liquid formulation with a solvent comprising/consisting of a mixture of ethanol and water which is administered via an (equine) inhalation device.

In a specific aspect of the present invention (ciclesonide or a pharmaceutically acceptable salt thereof or a composition comprising ciclesonide or a pharmaceutically acceptable salt thereof for the use in a method for treating an airways disease and/or a method of treatment with ciclesonide or a pharmaceutically acceptable salt thereof or a composition comprising ciclesonide or a pharmaceutically acceptable salt thereof) the airway disease is a pulmonary disease. In another aspect of the present invention the airway disease is selected from the group consisting of: recurrent airway obstruction (RAO), summer pasture associated obstructive pulmonary disease (SPAOPD), and inflammatory airway disease (IAD). In a preferred aspect of the present invention the airway disease is recurrent airway obstruction (RAO).

In another specific aspect of the present invention ciclesonide or a pharmaceutically acceptable salt thereof or a composition comprising ciclesonide or a pharmaceutically acceptable salt thereof is administered via an (equine) inhaler device. Preferably said inhaler device comprises: (a) a pressurized metered dose inhaler or an aqueous/ethanolic droplet inhaler such as the RESPIMAT® inhaler or another inhalation device using the RESPIMAT® aerosol-generating technology and (b) an adapter for equine use. In yet another specific aspect of the present invention ciclesonide or said pharmaceutically acceptable salt thereof or said composition comprising ciclesonide or said pharmaceutically acceptable salt thereof is a partially ethanolic formulation and is administered via an (equine) inhaler device.

In a further aspect of the present invention (ciclesonide or a pharmaceutically acceptable salt thereof or a composition comprising ciclesonide or a pharmaceutically acceptable salt thereof for the use in a method for treating an airways disease and/or a method of treatment with ciclesonide or a pharmaceutically acceptable salt thereof or a composition comprising ciclesonide or a pharmaceutically acceptable salt thereof) said ciclesonide or said pharmaceutically acceptable salt thereof or said composition comprising ciclesonide or said pharmaceutically acceptable salt thereof is administered at a dose of at least 900 µg ex inhaler, at least 1800 µg ex inhaler, or at least 2700 µg ex inhaler, preferably at least 2700 µg ex inhaler. In yet another aspect of the present invention said ciclesonide or said pharmaceutically acceptable salt thereof or said composition comprising ciclesonide or said pharmaceutically acceptable salt thereof is administered at a dose of 100 µg to 5000 µg ex inhaler, 450 µg to 2700 µg ex inhaler, 900 µg to 2700 µg ex inhaler, preferably at a dose of 900 µg to 2700 µg ex inhaler. According to a preferred aspect of the present invention ex inhaler is ex RESPIMAT® inhaler.

In another aspect of the present invention (ciclesonide or a pharmaceutically acceptable salt thereof or a composition comprising ciclesonide or a pharmaceutically acceptable salt thereof for the use in a method for treating an airways disease and/or a method of treatment with ciclesonide or a pharmaceutically acceptable salt thereof or a composition comprising ciclesonide or a pharmaceutically acceptable salt thereof) said ciclesonide or said pharmaceutically acceptable salt thereof or said composition comprising ciclesonide or said pharmaceutically acceptable salt this administered with 20 or fewer actuations per dose, preferably 12, 11, 10, 9, 8, 7, 6, 5, 4, 3, 2, or 1 actuations, most preferably it is administered using 8 or fewer actuations per dose.

In a specific aspect of the present invention the composition comprising ciclesonide or a pharmaceutically acceptable salt thereof is prepared for administration at a concentration of 0.7-3.1 g ciclesonide/100 mL or 1.0-3.1 g ciclesonide/100 ml inhalation solution. Preferably it is prepared for the administration with 20 or fewer actuations per dose, preferably 12, 11, 10, 9, 8, 7, 6, 5, 4, 3, 2, or 1 actuations per dose, most preferably the composition is prepared for the administration using 8 or fewer actuations per dose.

In a specific aspect of the present invention (ciclesonide or a pharmaceutically acceptable salt thereof or a composition comprising ciclesonide or a pharmaceutically acceptable salt thereof for the use in a method for treating an airways disease and/or a method of treatment with ciclesonide or a pharmaceutically acceptable salt thereof or a composition comprising ciclesonide or a pharmaceutically acceptable salt thereof) said ciclesonide or said pharmaceutically acceptable salt thereof or said composition comprising ciclesonide or said pharmaceutically acceptable salt thereof is administered in 1 to 3 doses per day, preferably 1 or 2 doses are administered per day/once daily. In another specific aspect of the present invention said ciclesonide or said pharmaceutically acceptable salt thereof or said composition comprising ciclesonide or said pharmaceutically acceptable salt thereof is administered once daily. In a further specific aspect of the present invention said ciclesonide or said pharmaceutically acceptable salt thereof or said composition comprising ciclesonide or said pharmaceutically acceptable salt thereof is administered in 1 to 4 doses per week (e.g. every 2. day, that is 3.5 doses per week).

In a specific aspect of the present invention the composition comprising ciclesonide or a pharmaceutically acceptable salt thereof is made/prepared with/for the administration of a concentration of 0.7-3.1 g ciclesonide/100 mL or 1.0-3.1 g ciclesonide/100 mL. Preferably it is prepared for the administration in 1 to 3 doses per day, preferably 1 or 2 doses per day. Preferably it is prepared for the administration of 1 to 2 doses once daily. In a further specific aspect of the present invention the composition comprising ciclesonide or a pharmaceutically acceptable salt thereof is prepared for the administration in 1 to 3 doses per week.

In yet another aspect of the present invention (ciclesonide or a pharmaceutically acceptable salt thereof or a composition comprising ciclesonide or a pharmaceutically acceptable salt thereof for the use in a method for treating an airways disease and/or a method of treatment with ciclesonide or a pharmaceutically acceptable salt thereof or a composition comprising ciclesonide or a pharmaceutically acceptable salt thereof), said ciclesonide or said pharmaceutically acceptable salt thereof or said composition comprising ciclesonide or said pharmaceutically acceptable salt thereof is administered over an extended time period of at least 1 week, at least 2, 3, 4, 5, 6, 7, 8, 9, or 10 weeks or more. In a preferred aspect of the present invention said ciclesonide or said pharmaceutically acceptable salt thereof or said composition comprising ciclesonide or said pharmaceutically acceptable salt thereof is administered in 1-2 doses daily over an extended time period. In a specific aspect said time period is at least 1 week, which can be extended to at least 2, 3, 4, 5, 6, 7, 8, 9, or 10 weeks or more. Preferably said ciclesonide or said pharmaceutically acceptable salt thereof or said composition comprising ciclesonide or said pharmaceutically acceptable salt thereof is administered in 1 or 2 doses daily over an extended period, whereby said period is preferably at least 1 week, which can be extended to at least 2, 3, 4, 5, 6, 7, 8, 9, or 10 weeks or more.

In a specific aspect of the present invention the composition comprising ciclesonide or a pharmaceutically acceptable salt thereof is prepared for the administration at a concentration of 0.7-3.1 g ciclesonide/100 mL or 1.0-3.1 g ciclesonide/100 mL inhalation solution. Preferably the composition comprising ciclesonide or a pharmaceutically acceptable salt thereof is prepared for the administration over an extended time period of at least 1 week, at least 2, 3, 4, 5, 6, 7, 8, 9, or 10 weeks or more. In a preferred aspect of the present invention the composition comprising ciclesonide or a pharmaceutically acceptable salt thereof is prepared for the administration in 1 or 2 doses daily over an extended time period of at least 1 week, at least 2, 3, 4, 5, 6, 7, 8, 9, or 10 weeks or more, most preferably the composition comprising ciclesonide or a pharmaceutically acceptable salt thereof is prepared for the administration in 1 dose daily over an extended period of at least 1 week, at least 2, 3, 4, 5, 6, 7, 8, 9, or 10 weeks or more.

Temporal variations in transpulmonary pressure ($\Delta P_L$) associated with the administration of dexamethasone (black bars) and three different doses of budesonide applied with the RESPIMAT® inhaler (450 µg (nozzle A): white bars, 900 µg (nozzle A): striped, 1800 µg (nozzle A): crossed) between days 0 and 14 (mean±SEM) (n=8), where SEM is "Standard Error of the Mean".

FIG. 2: BUDESONIDE STUDY

Temporal variations in breathing effort score associated with the administration of dexamethasone (black bars) and three different doses of budesonide applied with the RESPIMAT® inhaler (450 µg (nozzle A): white bars, 900 µg (nozzle A): striped, 1800 µg (nozzle A): crossed) between days 0 and 14 (mean±SEM) (n=8)

FIG. 3: BUDESONIDE STUDY

Temporal variations in serum cortisol associated with the administration of dexamethasone (black bars) and three different doses of budesonide applied with the RESPIMAT® inhaler (450 µg (nozzle A): white bars, 900 µg (nozzle A): striped 1800 µg (nozzle A): crossed) between days 0 and 14 (mean±SEM) (n=8)

FIG. 4: CICLESONIDE $1^{ST}$ STUDY

Temporal variations in transpulmonary pressure ($\Delta P_L$) associated with the administration of dexamethasone (black bars) and three different doses of ciclesonide applied with the RESPIMAT® inhaler (450 µg (nozzle A): white bars, 900 µg (nozzle A): striped, 1800 µg (nozzle A): crossed) between days 0 and 14 (mean±SEM) (n=8)

FIG. 5: CICLESONIDE $1^{ST}$ STUDY

Temporal variations in serum cortisol associated with the administration of dexamethasone (black bars) and three different doses of ciclesonide applied with the RESPIMAT® inhaler (450 µg (nozzle A): white bars, 900 µg (nozzle A): striped, 1800 µg (nozzle A): crossed) between days 0 and 14 (mean±SEM) (n=8)

FIG. 6A AND 6B: CICLESONIDE $2^{ND}$ STUDY

Figure 6A:
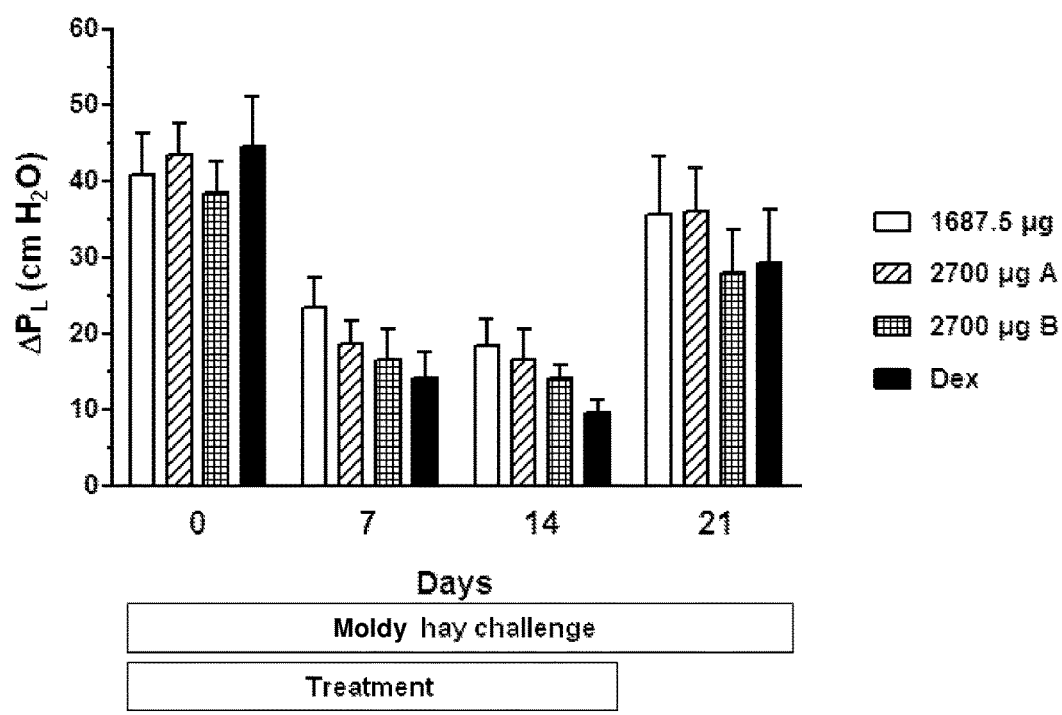

FIG. 6A: Temporal variations in transpulmonary pressure ($\Delta P_L$) associated with the administration of dexamethasone (black bars) and three different doses of ciclesonide applied with the RESPIMAT® inhaler (1687.5 µg (nozzle B): white bars, 2700 µg (nozzle A): striped, 2700 µg (nozzle B): crossed) between days 0 and 14 (mean±SEM) (n=8)

Figure 6B:
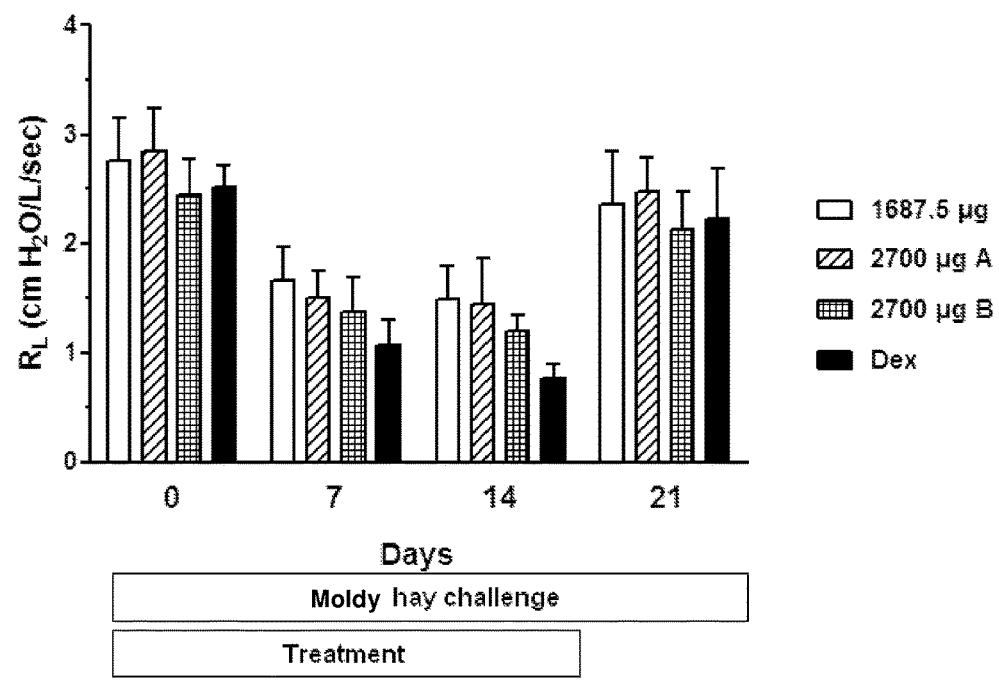

FIG. 6B: Temporal variations in lung resistance ($R_L$) associated with the administration of dexamethasone (black bars) and three different doses of ciclesonide applied with the RESPIMAT® inhaler (1687.5 µg (nozzle B): white bars, 2700 µg (nozzle A): striped, 2700 µg (nozzle B): crossed) between days 0 and 14 (mean±SEM) (n=8)

FIG. 7: CICLESONIDE $2^{ND}$ STUDY

Temporal variations in weighted clinical score associated with the administration of dexamethasone (black bars) and three different doses of ciclesonide applied with the RESPIMAT® inhaler (1687.5 µg (nozzle B): white bars, 2700 µg (nozzle A): striped, 2700 µg (nozzle B): crossed) between days 0 and 14 (mean±SEM) (n=8)

FIG. 8: CICLESONIDE $2^{ND}$ STUDY

Temporal variations in serum cortisol associated with the administration of dexamethasone (black bars) and three different doses of ciclesonide applied with the RESPIMAT® inhaler (1687.5 µg (nozzle B): white bars, 2700 µg (nozzle A): striped, 2700 µg (nozzle B): crossed) between days 0 and 14 (mean±SEM) (n=8)

DETAILED DESCRIPTION OF THE INVENTION

Both budesonide and ciclesonide are investigated and compared to dexamethasone in the same moldy hay challenge model. Both drugs are administered by the RESPIMAT® inhaler with an adapter for use with horses ("Equine Inhaler device") at different dose levels (see examples 1 to 3). Both molecules show a comparable efficacy to dexamethasone measured in lung function variables (transpulmonary pressure, lung resistance and lung elastance) and clinical score (breathing effort score and weighted clinical score) (see example 1 and 3). However, the blood levels of cortisol are different between budesonide and ciclesonide (see examples 1-3). The cortisol level is comparable between the highest dose of budesonide and dexamethasone after 14 days of treatment, showing a significant reduction in comparison to the baseline cortisol value (see example 1). In contrast, the cortisol level does not change significantly after the administration of the highest ciclesonide dose, whereas it is significantly reduced after the administration of dexamethasone compared to values prior to treatment (see example 3). In addition, complete blood count is investigated as well after 14 days treatment with dexamethasone and ciclesonide. Neutrophilia and lymphopenia are observed after the administration of dexamethasone in both studies (see Examples 2 and 3). In contrast, neutrophilia and lymphopenia are not observed after the administration of the different doses of ciclesonide.

Before describing the various aspects of the present invention it shall be noted that as used herein and in the appended claims, the singular forms "a", "an", and "the" include plural reference unless the context clearly dictates otherwise. Thus, for example, reference to "a preparation" includes a plurality of such preparations reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention. Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "ciclesonide" ((11β,16α)-16,17-[[(R)-Cyclohexylmethylene]bis(oxy)]-11-hydroxy-21-(2-methyl-1-oxopropoxy)pregna-1,4-diene-3,20-dione, $C_{32}H_{44}O_7$, $M_r$=540.7 g/mol) is well known in the art and means/describes a glucocorticoid used to treat asthma and allergic rhinitis in humans. It is marketed for application in humans under the brand name ALVESCO® for asthma and OM-NA-RIS®/OMNIAIR™ for hay fever in the US and Canada. Ciclesonide is a prodrug. It is transformed into the active metabolite C21-C21-desisobutyrylciclesonide (=desciclesonide) via hydrolysis by intracellular esterases in the lung. Ciclesonide is a non-halogenated glucocorticoid, which predominantly exists in its form as R-Enantiomer.

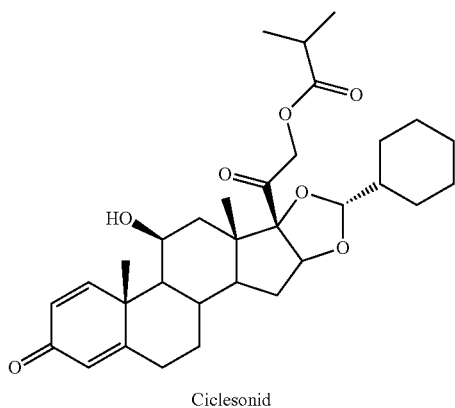

Ciclesonid

Formula II

Desciclesonid

The term "budesonide" is well known in the art and means/describes a glucocorticoid steroid for the treatment of asthma and non-infectious rhinitis (including hay fever and other allergies), and for treatment and prevention of nasal polyposis in humans. In addition, it is used for Crohn's disease (inflammatory bowel disease) in humans. Budesonide is known commercially as SYMBICORT®.

Budesonide

The term "dexamethasone" is well known in the art and means/describes a potent synthetic member of the glucocorticoid class of steroid drugs. It acts as an anti-inflammatory and immunosuppressant. When taken orally, it is 27 times more potent than the naturally occurring hormone cortisol and 7 times more potent than prednisone.

Dexamethasone

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can usually be readily prepared from the parent compounds using methods known in the art.

The term "equine" means of or belonging to the family Equidae, which includes the horses, asses, and zebras, preferably horses. In addition, the term "equine" encompasses also hybrids of members of the family Equidae (e.g. mules, hinnies, etc.)

The term "patient" or "subject" embraces mammals such as primates including humans. The term "patient" or "subject" as used herein relates specifically to horses, especially horses suffering from airway disease (particularly pulmonary disease), preferably from recurrent airway obstruction (RAO) also called heaves or equine COPD and/or summer pasture associated obstructive pulmonary disease (SPAOPD) also called Summer Pasture Associated Recurrent Airway Obstruction (SPARAO) and/or inflammatory airway disease (IAD), most preferably from RAO.

The term "airway disease" in horses means the following: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, chronic interstitial lung disease and upper respiratory tract functional disorders.

The term "pulmonary disease" means: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, or chronic interstitial lung disease.

The term "recurrent airway obstruction (RAO)" in horses means the following: a chronic syndrome of mature horses with reversible airway obstruction in the stable showing periods of labored breathing at rest during exacerbation.

The term "Summer Pasture Associated Obstructive Pulmonary disease (SPAOPD)" in horses means the following: a chronic syndrome, which shares many clinical and pathological similarities with RAO at rest on the pasture, suggesting similar pathogenesis, however, it is caused by different antigens.

The term "inflammatory airway disease (IAD)" in horses means the following: a chronic syndrome of horses showing poor performance or coughing or excess tracheal mucus without showing periods of labored breathing at rest.

The term "effective amount" as used herein means an amount sufficient to achieve a reduction of airway disease in a horse when ciclesonide is administered, preferably at a dosage as described herein. The progress of the therapy (improvement of airway disease, particularly pulmonary disease, preferably recurrent airway obstruction (RAO) and/or Summer Pasture Associated Obstructive Pulmonary disease (SPAOPD) and/or inflammatory airway disease (IAD), most preferably RAO as described herein) can be monitored by standard airway/pulmonary diagnosis, for example, by clinical examination, airway fluid cytology, endoscopy, lung function measurement, or blood-gas analysis.

The term "pharmaceutically acceptable derivative thereof" means but is not limited to pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

Dosage

The dosage regimen for the treatment of an equine using ciclesonide or a composition comprising ciclesonide (as an active compound) according to the present invention will, of course, vary depending upon known factors, such as the pharmacodynamic characteristics of the particular agent and its mode and route of administration; the species, age, sex, health, medical condition, and weight of the recipient (or patient); the nature and extent of the symptoms; the kind of concurrent treatment; the frequency of treatment; the route of administration, the renal and hepatic function of the patient, and the effect desired.

A physician or veterinarian can determine and prescribe the effective amount of the drug required to prevent, counter, or arrest the progress of the disorder.

In the context of the present invention the term "dose" means the delivered dose "ex inhaler". Ex inhaler comprises for example a pressurized metered dose inhaler (pMDI) or an aqueous/ethanolic droplet inhaler. A specific form of an aqueous/ethanolic droplet inhaler is, for example, the RESPIMAT® inhaler or another inhalation device using the RESPIMAT® technology.

The concentration of ciclesonide contained in the solution in the inhalation device ranges preferably from 0.7 to 3.1% m/V.

The systemic dose is determined by measuring the blood levels of the prodrug (ciclesonide) and the activated metabolite (desisobutyryl-ciclesonide) in case systemic exposure is relevant in the horse. A high systemic dose results in higher side effects for example reduction of cortisol serum levels.

In addition, radioisotope labeled ciclesonide (e.g., $^{99m}$Tc) can be used to examine the distribution of ciclesonide and its metabolites in the body, especially in the upper and lower airway tract. Based on the currently available scientific data, the dose of ciclesonide, when used for the indicated effects, will range between 200 and 5000 μg/horse (ex inhaler), preferably 400 to 4000 μg/horse (ex inhaler), even more preferred between 1000 and 3500 μg/horse (ex inhaler), most preferred between 1500 and 3100 μg/horse (ex inhaler). Those doses should be administered once, twice or three times per day, preferably once or twice daily. In a specific embodiment of the present invention those doses should be administered once a day.

In another specific embodiment of the present invention the dosage (such as the doses outlined above) may be split into or reduced to anywhere in between one dose once in two days up to one dose once in a week. The treatment is advisable in clinically apparent cases, both in acute as well as in chronic settings.

Administration

Suitable forms for "administration" are for example inhalation, parenteral or oral administration.

In the specific administration via the RESPIMAT® inhaler the content of the pharmaceutically effective ciclesonide should be in the range from 0.1 to 5% m/V, preferably 0.7 to 3.1% m/V or 1.0 to 3.1% m/V of the total composition, i.e. in amounts which are sufficient to achieve the dose range specified hereinafter.

When administered by inhalation ciclesonide may be given as an ethanolic solution or a solution containing a mixture of water and ethanol. Preferably, therefore, pharmaceutical formulations are characterized in that they comprise ciclesonide according to the preferred aspects above.

It is particularly preferred that ciclesonide is administered via inhalation/ex inhaler, preferably it is administered once or twice a day. Suitable formulations may be obtained, for example, by mixing ciclesonide with known excipients, for example water, pharmaceutically acceptable organic solvents such as mono- or polyfunctional alcohols (e.g. ethanol or glycerol), or refrigerants such as hydrofluoroalkanes (HFA), specifically HFA 227 and HFA 134a. For a liquid formulation, additional excipients for example hydrochloric acid or citric acid to adjust the [H$^+$] concentration may be added.

It is especially preferred that ciclesonide is administered by/via an aqueous/ethanolic droplet inhaler, for example the RESPIMAT® inhaler or another inhalation device using the RESPIMAT® aerosol-generating technology. Preferably ciclesonide is administered once or twice a day. For this purpose, ciclesonide has to be made available in a liquid solution which is suitable for the inhaler.

Most preferably the solvent in the liquid formulation (inhalation solution) comprises a mixture of ≥85% V/V ethanol and ≤15% V/V water, such as 90% V/V ethanol and 10% V/V water.

In a specific embodiment the formulation of ciclesonide is as follows:

TABLE 2

| Ingredient | Content |
| --- | --- |
| Ciclesonide | 0.7-3.1 g/100 mL |
| Hydrochloric acid | ad [H$^+$] = $10^{-3.5}$ to $10^{-5}$ mol/L |
| 90% V/V ethanol/water | ad 100 mL | where the concentration of hydrogen ions [H$^+$] can be measured, for example, by potentiometric titration.

A further aspect of the present invention is the application of the liquid formulation (inhalation solution) using the RESPIMAT® inhaler. This inhaler is disclosed for example in WO 97/12687, which is hereby incorporated therein. This inhaler can advantageously be used to produce the inhalable aerosols according to the invention. The dose of active substance delivered ex RESPIMAT® inhaler can be calculated from:
  the concentration of active substance in the liquid formulation [μg/μl],
  the "delivered volume", defined as the volume of liquid expelled from the RESPIMAT® inhaler per actuation M. The delivered volume ex RESPIMAT® inhaler has been found to be approximately 11.05 μl per actuation, according to the following formula:

$$\text{Dose [μg]} = \text{Concentration [μg/μl]} \cdot \text{Delivered Volume [μl]}$$

In a further aspect of the present invention the composition is administered via an (equine) inhaler device. The (equine) inhaler device preferably comprises the RESPIMAT® inhaler, which may be modified, and other parts to adapt the inhaler to equine use. In a preferred aspect the composition is a partially ethanolic formulation and is administered via an (equine) inhaler device. The dose emitted via the (equine) inhaler device is slightly lower than the dose ex RESPIMAT® inhaler.

EXAMPLES

The following examples serve to further illustrate the present invention; but the same should not be construed as a limitation of the scope of the invention disclosed herein.

Example 1

Budesonide is investigated in a cross-over, blinded moldy hay challenge study. Eight (8) RAO horses are examined in the study, which is divided into an acclimation and a treatment phase. Placebo for budesonide is administered a few times per inhalation via the Equine Inhaler device to all horses in the acclimation period. Budesonide and dexamethasone is administered to the horses in a cross-over design in the treatment phase. The horses are challenged by exposure to moldy hay throughout the acclimation and treatment periods. Budesonide is administered with the doses of 450 μg (2 actuations)/900 μg (4 actuations)/1800 (8 actuations) μg/horse (ex-RESPIMAT®) twice daily for 14 days per inhalation via the Equine Inhaler device. Nozzle A and a RESPIMAT® inhaler device not available commercially is used in the study. Nozzle A is the nozzle used with the commercially available RESPIMAT®. Dexamethasone is administered with a dose of 0.066 mg/kg per os, once daily for 14 days. Lung function variables (change in transpulmonary pressure, lung resistance and lung elastance), clinical score and blood parameters are examined during the study. The data is statistically analyzed using double repeated-measures ANOVA.

Figure 1:
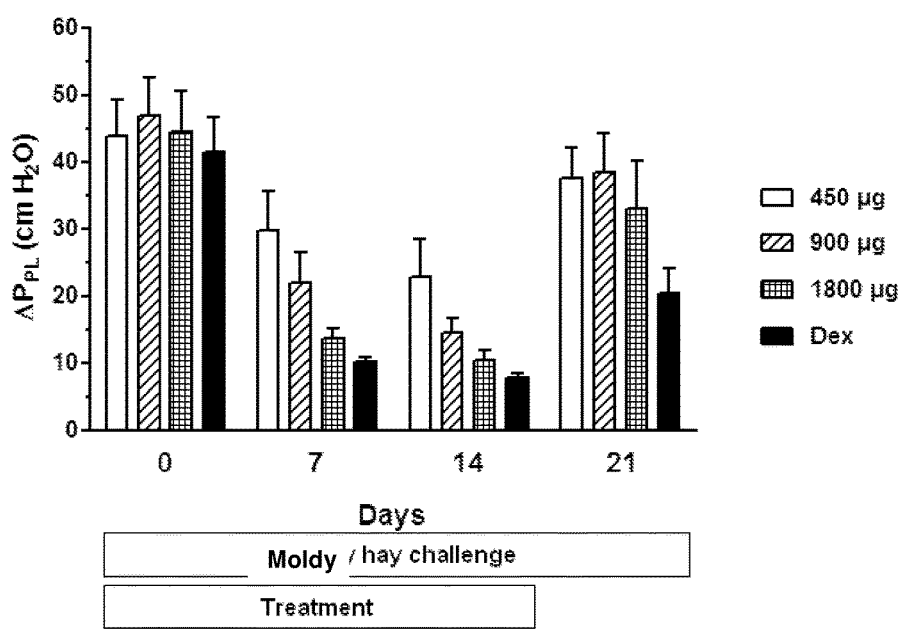
FIG. 1: BUDESONIDE STUDY
Figure 2:
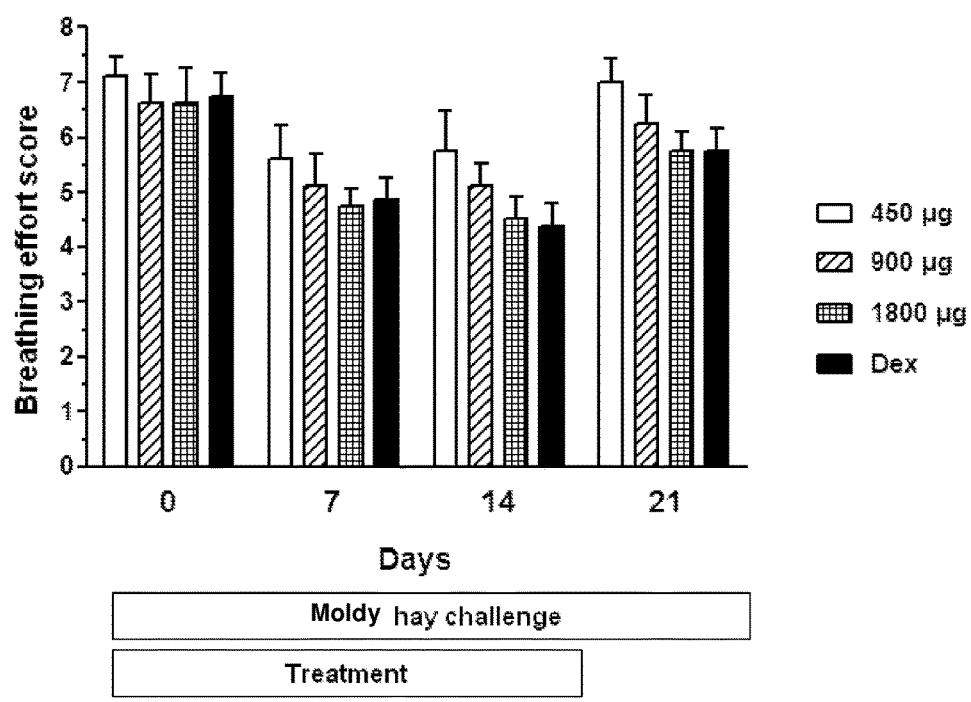
Figure 3:
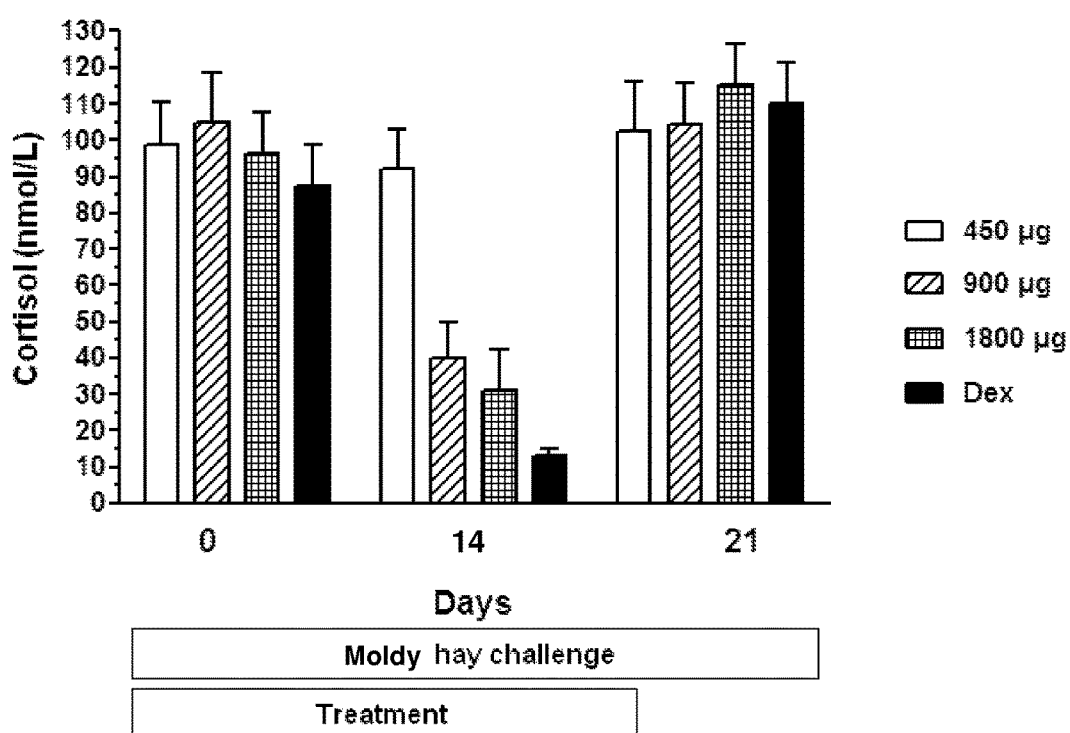

All lung function variables are significantly reduced in the highest dose budesonide (1800 μg/horse ex RESPIMAT®) and dexamethasone groups after 14 days treatment compared to pretreatment values (p≤0.0001) (see FIG. 1). There is no significant difference in the lung function variables between the highest dose budesonide (1800 μg/horse ex RESPIMAT®) and dexamethasone groups after 7 or 14 days treatment. The clinical score is significantly reduced after 7 and 14 days treatment in all three budesonide and the dexamethasone treatment groups compared to pretreatment values (p=0.002 to p<0.0001) (see FIG. 2). There is no significant difference in the clinical score between the highest and middle dose group of budesonide (900 and 1800 μg/horse ex RESPIMAT®) and the dexamethasone group after 7 and 14 days treatment. The cortisol levels in serum are significantly reduced in the highest and middle dose budesonide (900 and 1800 μg/horse ex RESPIMAT®) and dexamethasone groups after 14 days treatment compared to pretreatment values (p<0.0001) (see FIG. 3). There is no significant difference in the cortisol blood levels between the highest and middle dose group of budesonide (900 and 1800 μg/horse ex RESPIMAT®) and the dexamethasone group after 14 days treatment.

Example 2 (1st Ciclesonide Study)

Ciclesonide is investigated in a cross-over, blinded moldy hay challenge study. Eight (8) RAO horses are examined in the study, which is divided into an acclimation and a treatment phase. Placebo for ciclesonide is administered twice daily per inhalation via the Equine Inhaler device to all horses for 1 week in the acclimation period. Ciclesonide and dexamethasone are administered to the horses in a cross-over design in the treatment phase. The horses are challenged by exposure to moldy hay throughout the acclimation and treatment periods. Ciclesonide is administered with the doses of 450 μg (2 actuations)/900 μg (4 actuations)/1800 μg (8 actuations)/horse (ex-RESPIMAT®) twice daily for 14 days per inhalation via the Equine Inhaler device. Nozzle A and a commercially available RESPIMAT® is used in the study. Dexamethasone is administered with a dose of 0.066 mg/kg per os, once daily for 14 days. Lung function variables (change in transpulmonary pressure ($\Delta$PL), lung resistance (RL) and lung elastance (EL)), breathing effort score and blood parameters are examined during the study. The data is statistically analyzed using double repeated-measures ANOVA.

Figure 4:
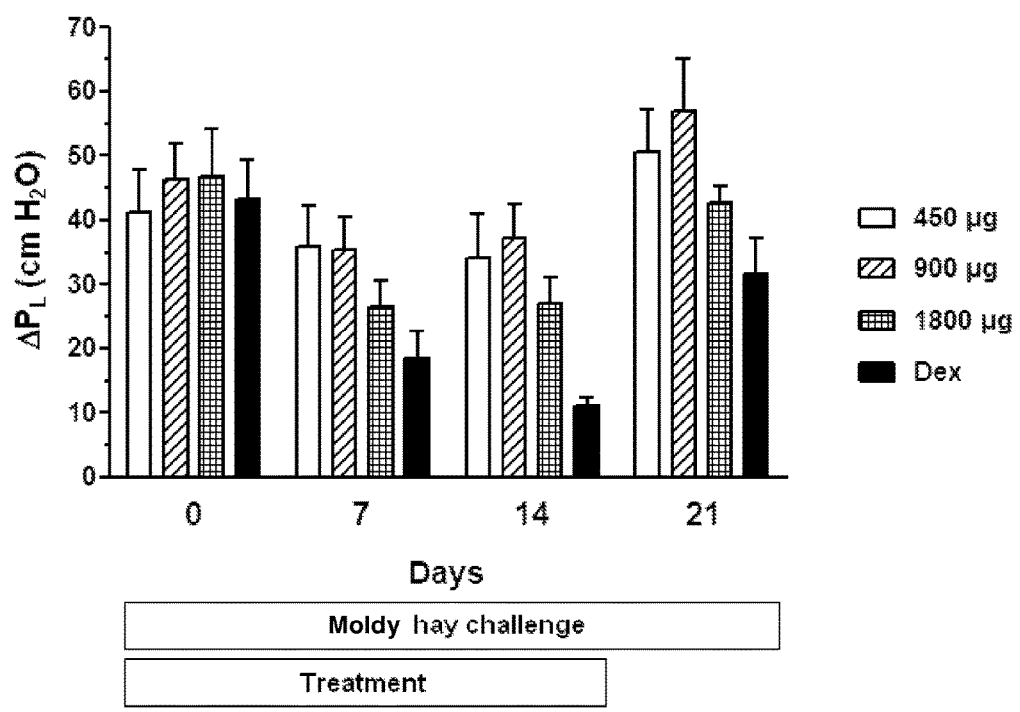

All lung function variables are significantly reduced in the dexamethasone group after 14 days treatment compared to pretreatment values ($p<0.0001$) (see FIG. 4). Only the highest dose ciclesonide group (1800 μg/horse ex RESPIMAT®) shows a statistically significant reduction in $\Delta$PL and EL after 14 days treatment compared to pretreatment values ($p=0.0005$ and $p=0.0004$). There is no significant difference in $\Delta$PL and EL between the highest dose ciclesonide (1800 μg/horse ex RESPIMAT®) and dexamethasone groups after 14 days treatment. The breathing effort score shows no significant changes in any of the treatment groups in any of the measured time points.

Figure 5:
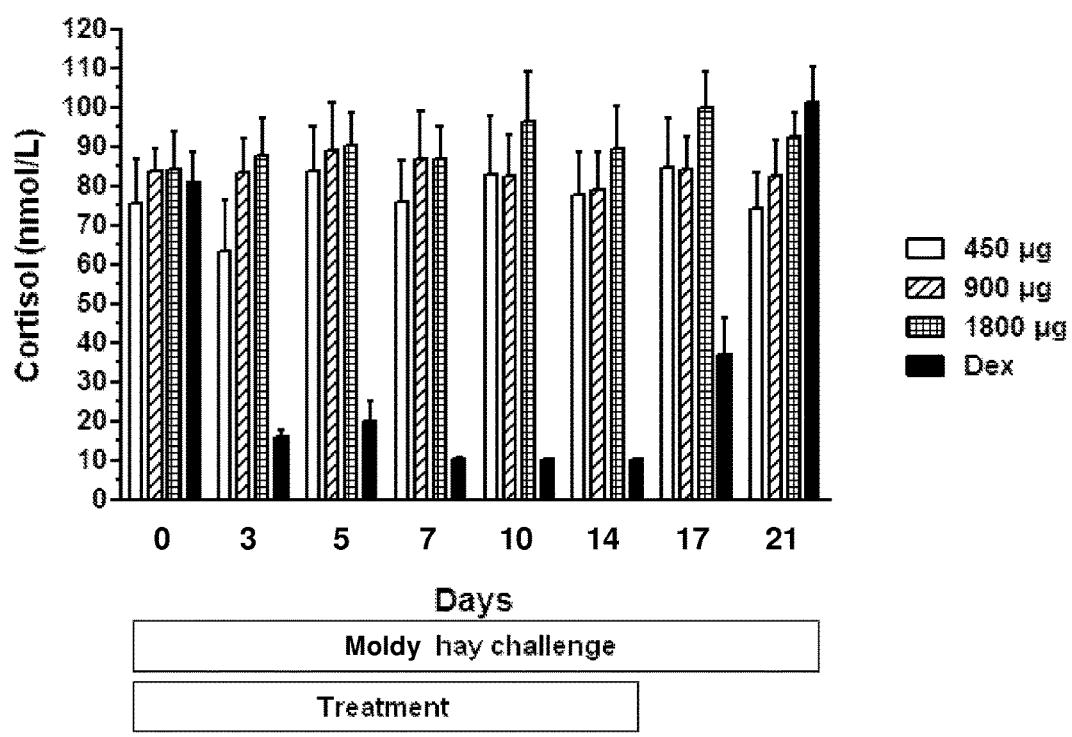

The serum cortisol levels are significantly reduced in the dexamethasone group compared to pretreatment values on days 3, 5, 7, 10, 14 and 17 following treatment initiation ($p<0.0001$) (see FIG. 5). There is no significant reduction in the serum cortisol levels in any of the ciclesonide treatment groups at any measured time points. The serum cortisol levels in the dexamethasone group are significantly reduced in comparison to any of the ciclesonide treatment groups on days 3, 5, 7, 10, 14 and 17 following treatment initiation ($p<0.0001$). The segmented neutrophil count is increased and the lymphocytes count is decreased after the administration of dexamethasone (see Example 4). There is no change in the counts of lymphocytes and no or minor increase in the counts of segmented neutrophils after the administration of ciclesonide.

Example 3 (2nd Ciclesonide Study)

Ciclesonide is investigated in a cross-over, blinded moldy hay challenge study. Eight (8) RAO horses are examined in the study, which is divided into an acclimation and a treatment phase. Placebo for ciclesonide is administered twice daily per inhalation via the Equine Inhaler device to all horses for 1 week in the acclimation period. Ciclesonide and dexamethasone are administered to the horses in a cross-over design in the treatment phase. The horses are challenged by exposure to moldy hay throughout the acclimation and treatment periods. Ciclesonide is administered with the doses of 1687.5 μg (5 actuations, nozzle B)/2700 μg (8 actuations, nozzle A)/2700 μg (8 actuations, nozzle B)/horse (ex-RESPIMAT®) twice daily for 14 days per inhalation via the Equine Inhaler device. The commercially available RESPIMAT® is used in the study. Nozzle A is the nozzle used with the commercially available RESPIMAT® inhaler. Nozzle B is a different nozzle resulting in a reduced spray time. Dexamethasone is administered with a dose of 0.066 mg/kg per os, once daily for 14 days. Lung function variables (change in transpulmonary pressure ($\Delta$PL), lung resistance (RL) and lung elastance (EL)), weighted clinical score and blood parameters are examined during the study. The data are statistically analyzed using double repeated-measures ANOVA.)

Figure 7:
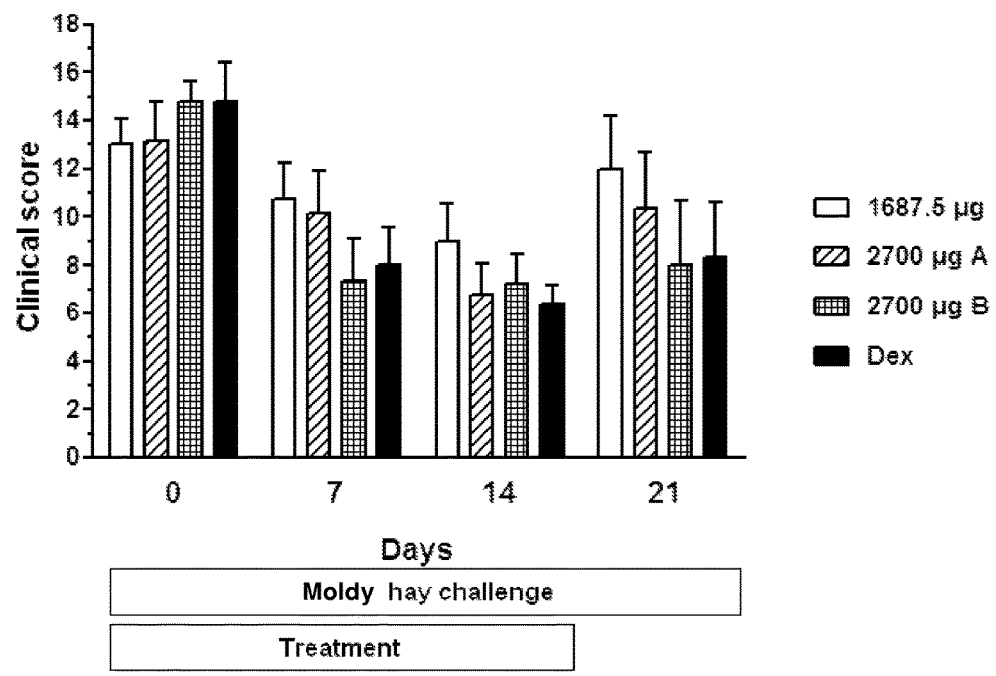
Figure 8:
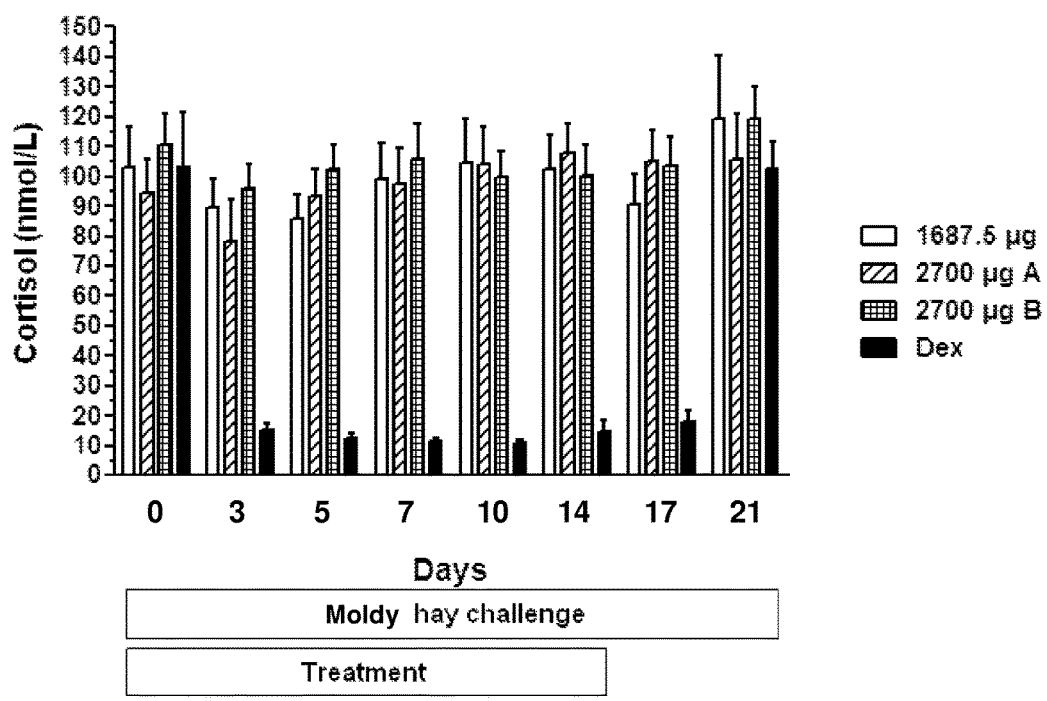

All lung function variables are significantly reduced in all ciclesonide and dexamethasone groups after 14 days treatment compared to pretreatment values ($p=0.0009$ to $p<0.0001$) (see FIGS. 6A and 6B). There is no significant difference in the lung function variables between all ciclesonide and dexamethasone groups after 7 or 14 days treatment. The weighted clinical score is significantly reduced after 14 days treatment in all three ciclesonide and the dexamethasone treatment groups compared to pretreatment values ($p=0.0001$ to $p<0.0001$) (see FIG. 7). There is no significant difference in the to weighted clinical score between the ciclesonide treatment groups and the dexamethasone group after 14 days treatment. The serum cortisol levels are significantly reduced in the dexamethasone group on days 3, 5, 7, 10, 14 and 17 following treatment initiation ($p<0.0001$) (see FIG. 8). There is no significant reduction in the serum cortisol levels in any of the ciclesonide treatment groups at any measured time points. The serum cortisol levels in the dexamathasone group are significantly reduced in comparison to any of the ciclesonide treatment groups on days 3, 5, 7, 10, 14 and 17 following treatment initiation ($p<0.0001$). The segmented neutrophil count is increased and the lymphocytes count is decreased after the administration of dexamethasone (see Example 4). There is no change in the counts of lymphocytes and no or minor increase in the counts of segmented neutrophils after the administration of ciclesonide.

Example 4

The segmented neutrophil counts and the lymphocyte counts are determined in the studies above: ciclesonide treatment versus dexamethasone treatment. For experimental setup and description of the conduction of the studies see Examples 2 and 3.

Concentration of segmented neutrophils and lymphocytes on day (D): D0, D14 and D21 in the treatment groups of dexamethasone and different doses of ciclesonide (n=8) (mean (SEM)

TABLE 3

| | Segmented neutrophils ($\times 10^9$/L) | | | Lymphocytes ($\times 10^9$/L) | | |
|---|---|---|---|---|---|---|
| | D 0 | D 14 | D 21 | D 0 | D 14 | D 21 |
| Dexamethasone (1st ciclesonide study) | 4.77 (1.34) | 6.16 (1.28) | 4.27 (1.23) | 2.10 (0.70) | 1.71 (0.52) | 1.76 (0.43) |

TABLE 3-continued

|  | Segmented neutrophils (×10⁹/L) | | | Lymphocytes (×10⁹/L) | | |
| --- | --- | --- | --- | --- | --- | --- |
|  | D 0 | D 14 | D 21 | D 0 | D 14 | D 21 |
| Dexamethasone (2nd ciclesonide study) | 4.82 (1.51) | 6.23 (1.45) | 4.82 (1.04) | 2.14 (0.62) | 1.73 (0.62) | 1.73 (0.34) |
| 450 µg ciclesonide | 4.66 (1.32) | 4.98 (1.75) | 5.48 (1.51) | 1.96 (0.36) | 1.97 (0.36) | 2.17 (0.50) |
| 900 µg ciclesonide | 5.24 (1.10) | 4.43 (1.06) | 4.91 (2.48) | 1.85 (0.28) | 2.03 (0.49) | 1.94 (0.34) |
| 1800 µg ciclesonide | 4.60 (1.33) | 5.41 (1.68) | 4.93 (1.10) | 1.95 (0.48) | 1.96 (0.64) | 2.06 (0.57) |
| 1687.5 µg ciclesonide | 4.51 (1.61) | 5.22 (2.54) | 4.55 (1.80) | 1.93 (0.48) | 1.94 (0.33) | 2.04 (0.41) |
| 2700 µg ciclesonide A | 4.91 (1.45) | 4.85 (1.10) | 4.41 (1.75) | 2.04 (0.57) | 2.14 (0.41) | 2.01 (0.43) |
| 2700 µg ciclesonide B | 4.23 (1.17) | 4.75 (2.02) | 4.84 (1.55) | 1.80 (0.45) | 1.74 (0.36) | 2.01 (0.57) |

Neutrophilia and lymphopenia is observed after the state of the art treatment with dexamethasone (see Table 2). In contrast, no alteration is observed in the immune system of horses measured by neutrophilia and lymphopenia after treatment for two weeks with different dose levels of ciclesonide (see Table 3).

Example 5

The concentration of ciclesonide and C21-C21-desisobutyrylciclesonide is determined in plasma samples in the above mentioned $2^{nd}$ ciclesonide study: ciclesonide treatment versus dexamethasone treatment. For experimental setup and description of the conduction of the study see Example 3. The plasma level of ciclesonide and C21-C21-desisobutyrylciclesonide are determined by high performance liquid chromatography coupled to tandem mass spectrometry. Plasma samples are collected prior to and 10, 30 min, 1, 2 and 4 h following ciclesonide administration on day 1 and 11 of the treatment phase with ciclesonide.

| Dose of ciclesonide (µg) | 0 min | 10 min | 30 min | 1 h | 2 h | 4 h |
| --- | --- | --- | --- | --- | --- | --- |
| Ciclesonide concentration on day 1 (nmol/L) | | | | | | |
| 1687.5 | <0.500 | 0.87 | <0.500 | <0.500 | <0.500 | <0.500 |
| 2700 A | <0.500 | 1.19 | 0.51 | <0.500 | <0.500 | <0.500 |
| 2700 B | <0.500 | 1.16 | 0.72 | <0.500 | <0.500 | <0.500 |
| Ciclesonide concentration on day 11 (nmol/L) | | | | | | |
| 1687.5 | <0.500 | 0.97 | <0.500 | <0.500 | <0.500 | <0.500 |
| 2700 A | <0.500 | 1.02 | 0.63 | <0.500 | <0.500 | <0.500 |
| 2700 B | <0.500 | 1.38 | 0.63 | <0.500 | <0.500 | <0.500 |
| C21-C21-desisobutyrylciclesonide concentration on day 1 (nmol/L) | | | | | | |
| 1687.5 | <0.250 | 0 | 0.38 | 0.34 | 0.38 | <0.250 |
| 2700 A | <0.250 | 0.35 | 0.45 | 0.47 | 0.3 | <0.250 |
| 2700 B | <0.250 | 0.28 | 0.59 | 0.48 | 0.34 | <0.250 |
| C21-C21-desisobutyrylciclesonide concentration on day 11 (nmol/L) | | | | | | |
| 1687.5 | <0.250 | 0.3 | 0.37 | 0.39 | 0.3 | <0.250 |
| 2700 A | <0.250 | 0.4 | 0.57 | 0.44 | 0.34 | <0.250 |
| 2700 B | <0.250 | 0.36 | 0.51 | 0.43 | 0.35 | <0.250 |

The concentration of ciclesonide is below the lower limit of quantification (0.5 nmol/L) in the plasma samples taken 1 h after drug administration. The concentration of C21-C21-desisobutyrylciclesonide is below the lower limit of quantification (0.25 nmol/L) in the plasma samples taken at 4 h after the administration of ciclesonide.

Example 6 ($3^{rd}$ Ciclesonide Study)

Ciclesonide is investigated in a cross-over, blinded moldy hay challenge study examining 8 RAO horses. Ciclesonide and placebo for ciclesonide are administered to the horses in a cross-over design. The horses are challenged by exposure to moldy hay to throughout the whole study. Ciclesonide is administered with the doses of 2700 µg, twice daily (8 actuations twice daily)/3712.5 µg, once daily in the morning (11 actuations once daily in the morning)/3712.5 µg, once daily in the evening (11 actuations once daily in the evening)/horse (ex-RESPIMAT®) for 14 days per inhalation via the Equine Inhaler device. Placebo for ciclesonide is administered with a dose of 0.0 µg ciclesonide/horse (ex-RESPIMAT®) twice daily for 14 days per inhalation via the Equine Inhaler device. The commercially available RESPIMAT® with nozzle B is used in the study (please see Example 3 for description of nozzle B). Lung function variables (change in transpulmonary pressure (ΔPL), lung resistance (RL) and lung elastance (EL)), weighted clinical score and blood parameters are examined during the study. The data are statistically analyzed using double repeated-measures ANOVA.

The lung function variables are significantly reduced in the ciclesonide treatment groups after 14 days treatment compared to the pretreatment values and compared to the placebo group as well. There is no significant reduction in the lung function variables of the placebo group after 14 days treatment compared to the pretreatment values.

Example 7 ($4^{th}$ Ciclesonide Study)

Ciclesonide is investigated in a baseline controlled, blinded study examining up to 3 IAD horses. Ciclesonide is administered with the dose of 2700 µg, twice daily (8 actuations twice daily)/horse (ex-RESPIMAT®) for 14 days per inhalation via the Equine Inhaler device. The commercially available RESPIMAT® with nozzle B is used in the study (please see Example 3 for description of nozzle B). Lung function variables using the impulse oscillometry system (respiratory resistance (Rrs) and reactance (Xrs)), weighted clinical score and blood parameters are examined during the study. The data are statistically analyzed using repeated-measures ANOVA.

REFERENCES

Kutasi O., Balogh N., Lajos Z., Nagy K., Szenci O.: Diagnostic approaches for the assessment of equine chronic pulmonary disorders. J. Eq. Vet. Sci. (2011) 31: 400-410

Coutil L. L:, Hoffman A. M., Hodgson J., Buechner-Maxwell V., Viel L., Wood J. L. N. and Lavoie J.-P.: Inflammatory airway disease of horses. J. Vet. Intern. Med. (2007) 21: 356-361

Dauvillier J., Felippe M. J. B., Lunn D. P., Lavoie-Lamoureux A., Leclere M., Beauchamp G., Lavoie J.-P.: Effect of long-term fluticasone treatment on immune function in horses with heaves. J. Vet. Intern. Med. (2011) 25: 549-557

Grahnén A., Jansson B., Brundin R. M., Ling-Andersson A., Lönnebo A., Johansson M. and Eckernäs S.-A.: A dose-response study comparing supression of plasma cortisol influenced by fluticasone propionate from Diskhaler and budesonide from Turbohaler. Eur. J. Clin. Pharm. (1997) 52: 261-267

Robinson N. E., Berney C., Behan A. and Derksen F. J.: Fluticasone propionate aerosol is more effective for prevention than treatment of recurrent airway obstruction. J. Vet. Intern. Med. (2009) 23 (6): 1247-1253

The invention claimed is:

1. A method of treating an airway disease in equines comprising administering to an equine an effective amount of ciclesonide or a pharmaceutically acceptable salt thereof or a composition comprising ciclesonide or a pharmaceutically acceptable salt thereof;
   wherein the ciclesonide or the pharmaceutically acceptable salt thereof or the composition comprising ciclesonide or the pharmaceutically acceptable salt thereof is administered at a dose of 100 µg to 5000 µg ex inhaler.

2. The method of claim 1, wherein the airway disease is a pulmonary disease.

3. The method of claim 1, wherein the airway disease is selected from the group consisting of recurrent airway obstruction (RAO), summer pasture associated obstructive pulmonary disease (SPAOPD), and inflammatory airway disease (IAD).

4. The method according to claim 3, wherein the airway disease is RAO.

5. The method claim 1, wherein the ciclesonide or the pharmaceutically acceptable salt thereof or the composition comprising ciclesonide or the pharmaceutically acceptable salt thereof is inhalable.

6. The method of claim 1, wherein the ciclesonide or the pharmaceutically acceptable salt thereof or the composition comprising ciclesonide or the pharmaceutically acceptable salt thereof is in a liquid formulation.

7. The method of claim 6, wherein the liquid formulation comprises one or more solvents selected from the group consisting of water, ethanol, hydrofluoroalkanes, hydrofluoroolefin, and excipients.

8. The method of claim 7, wherein the hydrofluoroalkanes are HFA 227, HFA 134a, and combinations thereof.

9. The method of claim 7, wherein the hydrofluoroolefin is HFO1234ze.

10. The method of claim 6, wherein the solvent in the liquid formulation is partially aqueous and partially ethanol.

11. The method of claim 10, wherein the solvent in the liquid formulation comprises of a mixture of ≥85% V/V ethanol and ≤15% V/V water.

12. The method of claim 10, wherein the solvent in the liquid formulation comprises 10% V/V water and 90% V/V ethanol.

13. The method of claim 6, wherein the ciclesonide or the pharmaceutically acceptable salt thereof or the composition comprising ciclesonide or the pharmaceutically acceptable salt thereof is administered via an inhaler device.

14. The method of claim 13, wherein the inhaler device comprises:
   a. a pressurized metered dose inhaler or a aqueous/ethanolic droplet inhaler comprising the RESPIMAT® inhaler or another inhalation device using the RESPIMAT® aerosol-generating technology; and
   b. an adapter for equine use.

15. The method of claim 6, wherein the ciclesonide or the pharmaceutically acceptable salt thereof or the composition comprising ciclesonide or the pharmaceutically acceptable salt thereof is a partially ethanolic formulation and is administered via an inhaler device.

16. The method of claim 15, wherein the ciclesonide or the pharmaceutically acceptable salt thereof or the composition comprising ciclesonide or the pharmaceutically acceptable salt thereof is administered at a dose of at least 900 µg ex inhaler, at least 1800 µg ex inhaler, or at least 2700 µg ex inhaler.

17. The method of claim 16, wherein the ciclesonide or the pharmaceutically acceptable salt thereof or the composition comprising ciclesonide or the pharmaceutically acceptable salt thereof is administered at a dose of 450 µg to 2700 µg ex inhaler.

18. The method of claim 16, wherein the ciclesonide or the pharmaceutically acceptable salt thereof or the composition comprising ciclesonide or the pharmaceutically acceptable salt thereof is administered at a dose of 900 µg to 2700 µg ex inhaler.

19. The method of claim 6, wherein the ciclesonide or the pharmaceutically acceptable salt thereof or the composition comprising ciclesonide or the pharmaceutically acceptable salt thereof is administered with less than 20 actuations per dose.

20. The method of claim 19, wherein the ciclesonide or the pharmaceutically acceptable salt thereof or the composition comprising ciclesonide or the pharmaceutically acceptable salt thereof is administered with 12, 11, 10, 9, 8, 7, 6, 5, 4, 3, 2, or 1 actuations per dose.

21. The method of claim 20, wherein the ciclesonide or the pharmaceutically acceptable salt thereof or the composition comprising ciclesonide or the pharmaceutically acceptable salt thereof is administered using 8 or fewer actuations per dose.

22. The method of claim 6, wherein the ciclesonide or the pharmaceutically acceptable salt thereof or the composition comprising ciclesonide or the pharmaceutically acceptable salt thereof is administered in 1 to 3 doses per day.

23. The method of claim 22, wherein the ciclesonide or the pharmaceutically acceptable salt thereof or the composition comprising ciclesonide or the pharmaceutically acceptable salt thereof is administered in 1 to 2 doses per day.

24. The method of claim 6, wherein the ciclesonide or the pharmaceutically acceptable salt thereof or the composition comprising ciclesonide or the pharmaceutically acceptable salt thereof is administered over a time period of at least 1 week.

25. The method of claim 24, wherein the ciclesonide or the pharmaceutically acceptable salt thereof or the composition comprising ciclesonide or the pharmaceutically acceptable salt thereof is administered over a time period of at least 10 weeks.

26. A method according to claim 1, wherein the composition comprises a solution including 0.7-3.1 g ciclesonide/100 mL.

27. A method of treating an airway disease in equines comprising administering to an equine an effective amount of ciclesonide or a pharmaceutically acceptable salt thereof or a composition comprising ciclesonide or a pharmaceutically acceptable salt thereof;
   wherein the ciclesonide or the pharmaceutically acceptable salt thereof or the composition comprising ciclesonide or the pharmaceutically acceptable salt thereof is administered at a dose of 1800 µg to 5000 µg ex inhaler.

* * * * *